United States Patent [19]

Bonnet et al.

[11] Patent Number: 5,713,928
[45] Date of Patent: Feb. 3, 1998

[54] PROCESS OF CONTROLLING A DUAL CHAMBER CARDIAC PACEMAKER

[75] Inventors: Jean Luc Bonnet, Vanves; Marcel Limousin, Montrouge, both of France

[73] Assignee: ELA Medical, Montrouge, France

[21] Appl. No.: 693,533

[22] Filed: Jul. 25, 1996

[30] Foreign Application Priority Data

Jul. 25, 1995 [FR] France ................. 95-09031

[51] Int. Cl.$^6$ ............................................... A61N 1/362
[52] U.S. Cl. ........................................... 607/9; 607/14
[58] Field of Search ........................... 607/9, 14, 25

[56] References Cited

U.S. PATENT DOCUMENTS

| | | |
|---|---|---|
| 4,343,311 | 8/1982 | Markowitz . |
| 4,344,437 | 8/1982 | Markowitz . |
| 4,378,020 | 3/1983 | Nappholz et al. . |
| 4,412,541 | 11/1983 | Schaldach et al. . |
| 4,429,697 | 2/1984 | Nappholz et al. . |
| 4,432,362 | 2/1984 | Leckrone et al. . |
| 4,467,810 | 8/1984 | Vollman . |
| 4,515,161 | 5/1985 | Wittkampf et al. . |
| 4,554,920 | 11/1985 | Baker, Jr. et al. . |
| 4,554,921 | 11/1985 | Boute et al. . |
| 4,712,556 | 12/1987 | Baker et al. . |
| 4,714,079 | 12/1987 | Hedberg et al. . |
| 4,781,194 | 11/1988 | Elmqvist . |
| 4,788,980 | 12/1988 | Mann et al. . |
| 4,890,617 | 1/1990 | Markowitz et al. . |
| 4,932,406 | 6/1990 | Berkovits . |
| 4,944,298 | 7/1990 | Sholder . |
| 4,967,746 | 11/1990 | Vandegriff . |
| 5,312,451 | 5/1994 | Limousin et al. ............... 607/9 |
| 5,374,280 | 12/1994 | den Dolk ....................... 607/14 |
| 5,540,726 | 7/1996 | Bonnet et al. ................. 607/14 |

FOREIGN PATENT DOCUMENTS 318304  5/1989  European Pat. Off. .

Primary Examiner—William E. Kamm
Assistant Examiner—George R. Evanisko
Attorney, Agent, or Firm—Orrick Herrington & Sutcliffe LLP

[57] ABSTRACT

A process for controlling a dual chamber cardiac pacemaker having a fallback mode of de-synchronization of the ventricular stimulation when the atrial rhythm exceeds an allowable level, and a mode of progressive re-synchronization in case of the return of the atrial rhythm to the allowable level. In the process:

(a) at each detection of an atrial depolarization, one defines a window of Detection of the Acceleration of the Atrial Rhythm (DAAR) whose duration is a function the preceding atrial rhythm, evaluated according to the duration of one or an average of several of preceding atrial intervals, (b) at the detection of the next atrial depolarization, one starts an Atrial Escape Interval (AEI), and (c) if this next atrial depolarization has occurred in the DAAR window, one commands if necessary a consecutive atrial stimulation according to the AEI thus defined. According to the present invention, in step (a), one adapts the duration of the DAAR window as a function of the preceding atrial rhythm in a manner to define a first window for a determined rapid atrial rhythm and a second window for a determined slow atrial rhythm. which allows a discrimination between atrial extrasystoles (AES) and physiological accelerations of the atrial rhythm.

34 Claims, 1 Drawing Sheet

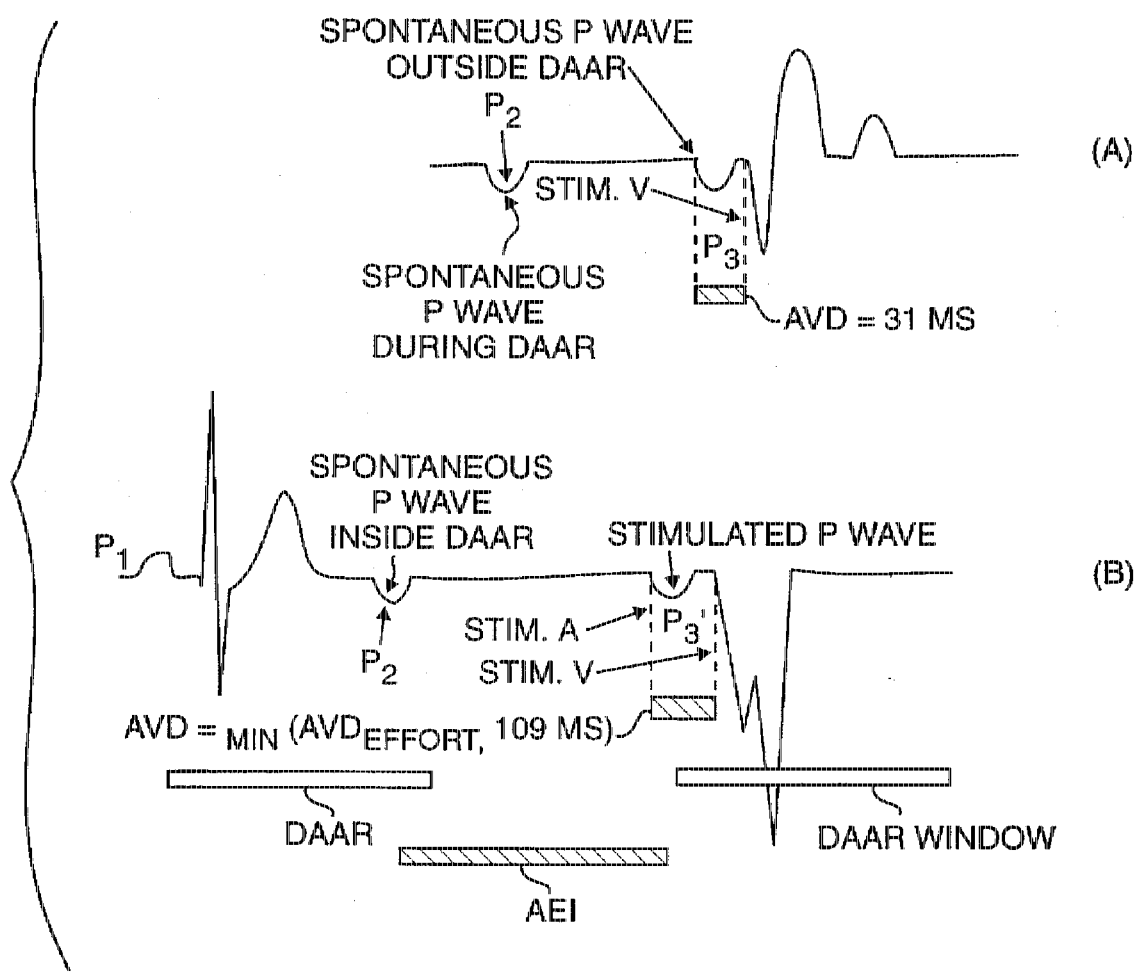

PROCESS OF CONTROLLING A DUAL CHAMBER CARDIAC PACEMAKER

FIELD OF THE INVENTION

This invention relates to a method of controlling the cardiac rhythm of a patient having a dual chamber cardiac pacemaker.

BACKGROUND OF THE INVENTION

The present invention concerns improvements in the processing of atrial extrasystoles (AES) in a cardiac pacemaker, as well as the related functioning in a "fallback" mode and the re-synchronization of ventricular stimulation to the sensed atrial rhythm at the end of a phase of fallback. Atrial extrasystoles (AES) are also known as premature atrial complexes ("PAC"s).

EP-A-0 488 840 and its corresponding U.S. Pat. No. 5,226,415, which are commonly assigned to the assignee of this invention ELA Medical, S.A., describe a mode of processing AES and a functioning in fallback, corresponding to what is implemented in the commercial pacemaker sold under the tradename CHORUS II 6234, of this same company. Essentially, this known process of processing AES is for use in a dual chamber cardiac pacemaker comprising a fallback mode of de-synchronization of the ventricular stimulation from the atrial rhythm when the atrial rhythm exceeds an allowable level, and then of progressive re-synchronization in the case of return of the atrial rhythm to the allowable level. The known process comprises the steps of:

(a) at each detection of an atrial depolarization, defining a window of Detection of the Acceleration of the Atrial Rhythm ("DAAR"), the duration of which is a function of the preceding atrial rhythm, evaluated according to the duration of one or more preceding atrial intervals (that is, the A—A interval from one atrial event to the following atrial event), and (b) at the detection of the next atrial depolarization, starting a delay for an Atrial Escape Interval ("AEI"), and (c) if this next atrial depolarization has occurred in the DAAR window, commanding, if necessary, a subsequent atrial stimulation according to the AEI thus defined.

The DAAR window is also known sometimes as a Window of Atrial Rhythm Acceleration Detection ("WARAD"). The reference to "commanding" a stimulation refers to generating the signals needed to initiate delivery of a stimulation pulse.

This operative mode is not, however, completely free from disadvantages. In the first place, because an AES is able to lead to a condition herein referred to as Trouble of the Atrial Rhythm ("ToAR"), it is important to recognize an AES with precision and to distinguish clearly between a real AES, i.e., an isolated event, and a simple physiological acceleration of the cardiac rhythm.

To this end, with regard to the known process for processing AES, the applicants have discovered that a DAAR window having a fixed duration that is 25% of the AA interval does not allow one to discriminate well between a physiological atrial acceleration (beginning of an "effort") and an isolated AES, and thus can result in a less desirable response of the pacemaker device; and further, in the case of an isolated AES, the Atrio-Ventricular Delay (AVD) of 31 ms that follows this AES is poorly tolerated by the patient.

In the second place, as the inventors also recognized, in case of a possible ToAR condition, to avoid that the possible ToAR condition becomes established, it is necessary to modify the behavior of the pacemaker following the detection of an AES. But, at the detection of an Atrial Fibrillation (AF) condition, the device commutes its mode of functioning from a DDD mode to a VVI mode (this implements a mode of fallback); in case of ultimate loss of the detection of atrial depolarizations, the pacemaker commutes to the DDD mode and the analysis that it performs at this stage does not allow it to change to the VVI mode; finally, at the end of the fallback mode, that is to say when the frequency of the atrial rhythm falls below the maximal synchronization frequency, there is a re-synchronization of ventricular stimulation to the atrial rhythm, but the delay until the device returns to the DDD operation is sometimes too long, which can favor a retrograde conduction or a bradycardia, with a consequent risk of return the ToAR condition.

OBJECTS AND SUMMARY OF THE INVENTION

It is, therefore, an object of the present invention to propose a process of processing AES and functioning in fallback and re-synchronization that overcomes the aforementioned disadvantages found in the known devices. The process of the invention is of the general type developed above, disclosed, for example, in EP-A-0 488 840 and its counterpart, U.S. Pat. No. 5,226,415, the latter of which is fully incorporated herein by reference in its entirety.

The improvement brought by the present invention comprises, with resect to the aforementioned step (a), in which the duration of the DAAR window is a set function of the preceding atrial rhythm, modifying the selection of the DAAR window in a manner to define a first window for a rapid atrial rhythm and a second window for a slow atrial rhythm, thereby to allow an improved discrimination between an atrial extrasystole ("AES") and physiological accelerations of the atrial rhythm. For convenience, the first window also may be referred to as the "long" or "relatively long" window, and the second window also may be referred to as the "short" or "relatively short" window.

In one embodiment, the invention thus operates to determine if the preceding atrial rhythm is rapid or slow. This may be achieved by determining an atrial rhythm and comparing the determined atrial rhythm to a threshold, such that a first or long window is selected when the atrial rhythm exceeds the threshold, and a second or short window is selected otherwise.

In one embodiment, the duration of the DAAR window is set equal to a fraction of the interval separating two successive preceding physiological atrial depolarizations. In an alternate embodiment, the duration of the DAAR window is set equal to a fraction of an average of a predetermined number of intervals separating two successive preceding physiological atrial depolarizations. In either of these two embodiments, the aforementioned fraction is preferably approximately 62.5% when one defines a short window, and approximately 75% when one defines a long window.

Another embodiment of the present invention concerns the aforementioned step (c), which is modified wherein, if one detects an atrial depolarization inside the DAAR window, and if, inside the AEI triggered by this atrial depolarization, one does not detect another consecutive atrial depolarization, then: (i) it is considered that there is an isolated AES; (ii) the atrium is stimulated at the end of the AEI; and (iii) a long Atrio-Ventricular Delay ("AVD") is set. In the opposite case in which a second consecutive atrial depolarization is sensed in the DAAR window, then: (i) it is considered that there is a suspicion of Trouble of the Atrial Rhythm (ToAR) condition; (ii) the device triggers a procedure of analyzing the atrial rhythm and a confirmation/non-confirmation of the suspected ToAR condition; and (iii) a short AVD is set. The short AVD is of a shorter duration than that of the long AVD.

In this last case, the duration of the long AVD is preferably determined as a function of the preceding cardiac rhythm, considering if need be, in addition a signal delivered by a sensor of a representative physiological parameter of the activity or effort level of the patient (commonly known as a rate responsive or enslavement parameter). Preferably, the AVD is determined as a function of the atrial rhythm which affects the ventricular rhythm. The duration of the long AVD is advantageously determined as a function of the signal delivered by this sensor, but limited to a predetermined limit value. The duration of the short AVD is preferably a fixed duration, related to the pre-programmed minimal interval between successive ventricular stimulations.

Also, with regard to step (c), the present invention provides that if an atrial depolarization is detected inside the DAAR window, and if, inside the AEI triggered by this atrial depolarization, one detects at least one other consecutive atrial depolarization, then it is considered that there is a suspicion of ToAR condition. In response, one releases a procedure of analyzing the atrial rhythm and a confirmation/non-confirmation of the suspected ToAR as follows. If, during the analysis of the atrial rhythm, one has a majority proportion of $x_1\%$ of cardiac cycles during $M_1$ successive cycles verifying the criterion of suspicion of ToAR, or a majority proportion of $x_2\%$ of cardiac cycles during $M_2$ successive cycles verifying the criterion of suspicion of ToAR, with $M_2>M_1$ and $x_2\%<x_1\%$, then one confirms the presence of a ToAR condition. If at the end of the procedure of analysis one has thus confirmed the presence of a ToAR condition, then from the atrial rhythm one commutes the pacemaker to a fallback operating mode in which the ventricular stimulation is de-synchronized from the atrial rhythm. Suitable operating conditions are advantageously, $M_2=2*M_1$, notably $M_1=32$ and $M_2=64$, and $x_1\%=87.5\%$ and $x_2\%=56\%$ approximately.

Also, with respect to step (c), the alternative embodiment of the present invention provides that if an atrial depolarization is detected inside the DAAR window and if, inside the AEI released by this atrial depolarization, one detects at least one other consecutive atrial depolarization, then it is considered that there is a suspicion of ToAR condition and one releases a procedure of analyzing the atrial rhythm and a confirmation/non-confirmation of the ToAR condition.

In this embodiment, if at the end of the analysis procedure one confirms the maintenance of a ToAR condition, then one commutes the pacemaker to a fallback operating mode in which the ventricular stimulation is de-synchronized from the atrial rhythm, and one releases a new procedure of analyzing the atrial rhythm to determine whether or not there is maintenance of the ToAR condition. If, during this new procedure of analyzing the atrial rhythm one detects the disappearance of the ToAR condition, then one commutes the pacemaker to an operating mode in which there is a progressive re-synchronization of the ventricular stimulation to a synchronized stimulation, and one releases a procedure of ventricular and atrial rhythm analysis and confirmation of the disappearance of the ToAR condition. If, during this procedure of ventricular and atrial rhythm analysis, one confirms the disappearance of the ToAR condition, then one commutes the pacemaker to a synchronized mode with dual-chamber stimulation (a DDD mode).

SUMMARY OF THE DRAWING

Further advantages features and characteristics of the present invention will become apparent from the following detailed discussion, made in reference to the annexed drawing, which is a diagram illustrating an embodiment of invention and the different delay intervals involved in the process of the invention in case of an AES.

DETAILED DESCRIPTION OF THE INVENTION

Referring to the drawing, the diagram A on the top corresponds to a spontaneous P wave $P_2$ occurring outside the DAAR window, while the diagram B on the bottom corresponds to the absence of such a spontaneous P wave, resulting in the release of an atrial stimulation by the device. The employment of "fallback" is based on the capacity of the device to differentiate normal sinusal (atrial) activity from an atrial extrasystole (AES). The DAAR window is employed to make this differentiation. The DAAR window is a period that starts on an atrial event (stimulated or spontaneous) and lasts 75% of the preceding atrial interval if the preceding atrial interval corresponds to an atrial rhythm that is greater than or equal to a threshold, e.g., 80 $min^{-1}$, or 62.5% of the preceding atrial interval if it corresponds to a rhythm below the threshold, 80 $min^{-1}$.

Preferably, if the preceding atrial interval was stimulated or decelerated by more than 25% in relation to the last atrial cycle, then the DAAR window is set equal to 75% or 62.5% of the average of the last eight cycles recognized as coming from the sinus, as the case may be. As used herein, a normal sinus activity is defined as a spontaneous (detected) atrial event that occurs outside the DAAR window, and an AES is defined as a spontaneous (detected) atrial event detected in (or during) the DAAR window.

In accordance with the invention, when an AES is detected, one does not start an Atrio-Ventricular Delay (AVD), one does not stimulate the ventricle (Stim. V) and one recycles the Atrial Escape Interval (AEI) to a value equal to the value of the DAAR window. By recycling the AEI, one advantageously avoids a premature atrial stimulation that could induce an atrial arrhythmia, and one provides the time that would be needed to detect another following trial event in the case of atrial arrhythmia.

The Case Of An Isolated AES

With reference to part B of the figure, after the detection of an AES ($P_2$) (that is the atrial depolarization detected during a DAAR window following a spontaneous atrial event $P_1$, typically a sinusal event), one recycles the AEI as noted. If no atrial event is detected before the end of the AEI, the atrium is stimulated (Stim.A, $P_3'$) and the AVD of effort (that is the AVD determined based on a sensed physiological parameter representative of patient effort or activity) is applied if it is less than or equal to 109 ms, and otherwise a AVD of 109 ms is applied. The utilization of a short AVD minimizes the excessive lengthening of the ventricular escape interval. The next DAAR window is then set equal to 75% or 62.5% of the average of the eight preceding sinusal cycles.

Case of a Trouble of the Atrial Rhythm (ToAR)

With reference to diagram A of the figure, if an atrial activity $P_3$ is detected after the AES $P_2$ and before the end of the AEI, one enters a phase of suspicion of ToAR. An AVD of 31 ms is set (released) in response to an atrial detection $P_3$ during the AEI.

On the other hand, if an atrial stimulation is delivered at the end of the AEI (Stim.A at the bottom diagram B), the AVD of effort is then applied if it is less than or equal to 109 ms, and otherwise an AVD of 109 ms is applied. The ventricular stimulation frequency is thus limited to 120 min$^{-1}$, or to the programmed value of the maximal stimulation frequency if it less than 120 min$^{-1}$. In this case, the value of the DAAR window is the same one as was used before the entry to the phase of suspicion of a ToAR condition.

Thus, when an atrial activity is detected during the DAAR window, one recycles the delay of atrial detection to 31 ms before the end of the minimum stimulation interval (that is, the interval corresponding to the limitation of ventricular stimulation frequency). Thus, according to the frequency of the ToAR, one insures a stable Wenkebach functioning in N:1. The ventricular stimulation is limited to 120 min$^{-1}$ or to the programmed maximal stimulation frequency, if the latter is lower.

Suspicion of ToAR by the Sensor

In accordance with the present invention, the use of a sensor producing a rate responsive pacing frequency allows the device to detect a trouble in the atrial rhythm that might have escaped triggering a suspicion of ToAR by using only the DAAR window. One considers that a cardiac cycle is in phase of suspicion of ToAR by the sensor if the atrial rhythm is greater than or equal to a first predetermined limit, e.g., 120 min$^{-1}$ while the rate responsive pacing frequency (also referred to as a frequency of enslavement) is less than a second predetermined limit, 98 min$^{-1}$. Preferably, this feature is automatically employed in a pacemaker which is programmed to employ a fallback mode and a sensor which produces a rate-responsive frequency. The sensor, as noted, may be of any of the kind known to detect patient activity or effort mechanically or physiologically and the term "physiological parameter" is used herein generically to encompass the different possibilities.

Confirmation of a ToAR Condition

In accordance with the present invention, the presence of a ToAR condition may be confirmed as follows. For a given number of cardiac cycles, one counts the number of cycles that are in a phase of suspicion of ToAR, and where appropriate, the number of cycles in a phase of suspicion of ToAR by the sensor. Typically, the number of cardiac cycles monitored is 32, although other values may be used. A ToAR condition is then confirmed if one of the three following conditions is verified:

(1) over the last group of 32 cycles, 28 cycles or more are in a phase of suspicion of ToAR (this is a case of a ToAR with a good atrial detection), (2) over the two last groups of 32 cycles, 18 cycles or more per group are in a phase of suspicion of ToAR (this is a case of a ToAR with medium atrial detection), (3) over the four last groups of 32 cycles, 24 cycles or more per group are in phase of suspicion of ToAR by the sensor (case of a ToAR that starts slowly and that is not detected by the DAAR window.

Fallback

The present invention implements operation in a fallback mode as follows. When a ToAR condition is confirmed, the device then functions in a conventional VDI mode. The ventricular escape interval VEI is lengthened by 31 ms every 12 cycles until the frequency of stimulation reaches the base frequency, the rest frequency or the frequency of enslavement (if the mode of enslavement is RRauto, RRfigee, DDD/VVIRauto or DDD/VVIRfigee). If no atrial activity is detected, one stimulates the atrium and the ventricle with an AVD equal to the AVD of effort if it is less than 109 ms; otherwise, an AVD of 109 ms is used.

It is an object of fallback to seek an atrio-ventricular synchronization as soon as the ToAR condition stops. Thus, the atrial frequency and the ventricular frequency is measured every 12 cardiac cycles. As long as one of these two frequencies is greater than the predetermined limit of 120 min$^{-1}$ or the programmed maximal stimulation frequency (if it is below 120 min$^{-1}$), the device remains in a fallback mode. As soon as both the ventricular and atrial frequencies become less than 120 min$^{-1}$ or the programmed maximal stimulation frequency (if it is less than 120 min$^{-1}$), one shortens the ventricular escape interval by 63 ms every 12 cycles until it reaches the atrial frequency (or the frequency of enslavement). The atrium and ventricle are then re-synchronized.

It is noted that a selected number of cardiac cycles other than 12 may be used. One will note furthermore that in the case that the mode of enslavement is set to DDD/VVIRauto or DDD/VVIRfigee, then the mode of functioning is not enslaved as long as the atrial rhythm is normal. As soon as one detects a ToAR condition, the enslavement is then applied during the phase of fallback.

Finally, if the mode of enslavement is DD/VVIRauto, the suspicion of ToAR by the sensor is not applied. The references to the rate responsive (enslavement) modes RRauto, RRfigee, DDD/VVIRauto and DDD/VVIRfigee are to the selectable modes of a rate responsive dual chamber pacemaker available from ELA Medical, under the trade name CHORUM 7334, which device evolved from an experimental prototype employing the present invention.

One skilled in the art will appreciate that the present invention can be practiced by other than the described embodiments, which are presented for purposes of illustration and not of limitation, and the numbers used in the described embodiments are exemplary and not limiting and may be varied without departing from the present invention.

We claim:

1. A process of controlling a dual chamber cardiac pacemaker operable to sense atrial and ventricular depolarizations, to stimulate an atrium and a ventricle, and to determine an atrial rhythm based on an interval between successive sensed atrial depolarizations and having a fallback mode of de-synchronization of a ventricular stimulation when the atrial rhythm exceeds an allowable level, and a mode of progressive re-synchronization in case of a return of the atrial rhythm to the allowable level comprising:

(a) sensing an atrial depolarization, defining a window of Detection of the Acceleration of the Atrial Rhythm (DAAR) in response to a sensed atrial depolarization, said DAAR having a duration that is a function of a preceding determined atrial rhythm, and further comprising at least one of the preceding intervals between successive sensed atrial depolarizations;

(b) sensing a next atrial depolarization, and in response thereto, starting a delay of an Atrial Escape Interval (AEI); and (c) determining if said next sensed atrial depolarization has occurred in the defined DAAR window duration, and commanding if necessary a following atrial stimulation according to the started AEI delay, wherein the method step (a) further comprises adapting the duration of the DAAR window as a function of the preceding atrial rhythm and selecting a first DAAR window duration for a rapid atrial rhythm and a second DAAR window duration for a slow atrial rhythm, and discriminating between atrial extrasystoles (AES) and a physiological acceleration of the atrial rhythm based on said selected DAAR window duration.

2. The process of claim 1 further comprising providing a threshold, comparing the atrial rhythm to the threshold and selecting the first DAAR window duration when the preceding atrial rhythm exceeds the threshold and the second DAAR window duration otherwise.

3. The process of claim 1, further comprising setting the duration of the DAAR window equal to a fraction of the interval separating two preceding successive physiological atrial depolarizations.

4. The process of claim 3, further comprising setting the fraction to approximately 62.5% when defining a second DAAR window duration and approximately 75% when defining a first DAAR window duration.

5. The process of claim 1, further comprising setting the duration of the DAAR window equal to a fraction of an average of a predetermined number of intervals separating two preceding successive physiological atrial depolarizations.

6. The process of claim 4, further comprising setting the fraction to approximately 62.5% when defining a second DAAR window duration and approximately 75% when defining a first DAAR window duration.

7. The process of claim 1, in which, in step (c), in response to determining that said next sensed atrial depolarization is inside the DAAR window:

if, inside the started AEI delay released by said next atrial depolarization, one does not detect another consecutive atrial depolarization:
(i) determining that there is an isolated atrial extra systole (AES), (ii) stimulating the atrium at the end of the AEI, and (iii) defining a long Atrio-Ventricular Delay (AVID); and in the opposite case:
(i) determining that there is a suspicion of Trouble of the Atrial Rhythm (ToAR) condition, initiating a procedure of analysis of the atrial rhythm and confirmation/non-confirmation of the suspicion of ToAR condition, and (ii) defining a short AVD having a shorter duration than the long AVD.

8. The process of claim 7, further comprising determining a duration of the long AVD as a function of the preceding atrial rhythm.

9. The process of claim 7, further comprising providing a signal representative of a physiological parameter of a patient's activity or effort and determining a duration of the long AVD as a function of the preceding atrial rhythm and the signal.

10. The process of claim 9, further comprising limiting the duration of the long AVD to a predetermined limit value.

11. The process of claim 7, further comprising determining a duration of the short AVD as a fixed duration corresponding to a minimal pre-programmed period of the ventricular stimulation.

12. The process of claim 1, in which:
in step (c), in response to sensing said next atrial depolarization inside the selected DAAR window duration, and in response to sensing at least one other consecutive atrial depolarization inside the AEI started by said next sensed atrial depolarization, considering that there is a suspicion of Trouble of the Atrial Rhythm (ToAR) condition, and releasing a procedure of analysis of the atrial rhythm and confirmation/non-confirmation of the suspicion of ToAR, counting, in response to the released analysis procedure of the atrial rhythm, a number of cardiac cycles, and determining whether or not there exists one of a majority proportion of $x_1\%$ of the cardiac cycles on $M_1$ successive cycles verifying the suspicion of ToAR, and a majority proportion of $x_2\%$ of the cardiac cycles on $M_2$ successive cycles verifying the suspicion of ToAR, with $M_2 > M_1$ and $x_2 < x_1$;

confirming the presence of a ToAR condition in response to said determining step; and, commuting the pacemaker to a mode of de-synchronized ventricular stimulation in response to said confirmed ToAR condition.

13. The process of claim 12, further comprising selecting $M_2 32\ 2*M_1$.

14. The process of claim 13, wherein $M_1=32$ and $M_2=64$, and $x_1\%=87.5\%$ and $x_2\%=56\%$ approximately.

15. The process of claim 1 further comprising providing said pacemaker with a dual chamber stimulation mode, in which:

in step (c), in response to detecting said next sensed atrial depolarization inside the selected DAAR window duration and in response to detecting at least one other consecutive atrial depolarization inside the AEI started by said next sensed atrial depolarization, considering that there is a suspicion of Trouble of the Atrial Rhythm (ToAR) condition and releasing a procedure of analysis of the atrial rhythm and confirmation/non-confirmation of the suspicion of ToAR condition;

in response to the released procedure of analysis, confirming the maintenance of a ToAR condition, commuting the pacemaker to operating in a mode of de-synchronized ventricular stimulation in response to a confirmed maintenance of a ToAR condition, and releasing a procedure of analysis of the atrial rhythm for maintenance of the ToAR condition;

detecting a disappearance of the ToAR condition, in response to the released procedure of analysis of the atrial rhythm for the maintenance of the ToAR condition, commuting the pacemaker to operate in a mode of progressive re-synchronization of the ventricular stimulation to a synchronized stimulation, and releasing a procedure of ventricular and atrial rhythm analysis and confirmation of the disappearance of the ToAR condition;

confirming a disappearance of the ToAR condition in response to said released procedure of ventricular and atrial rhythm analysis, and commuting the pacemaker to operate in a mode synchronized with the dual chamber stimulation mode.

16. A method for controlling a dual chamber pacemaker having atrial and ventricular depolarization monitoring circuits and atrial and ventricular stimulating circuits and a fallback operating mode in which the stimulation of the ventricles is desynchronized from an atrial rhythm comprising:

a. monitoring the spontaneous and stimulated atrial depolarization events as p waves;

b. monitoring stimulated and spontaneous ventricular depolarization events;

c. determining a ventricular rhythm from the monitored ventricular depolarization events;

d. detecting a first spontaneous P wave;

e. determining an atrial rhythm as a function of a pair of consecutive P waves;

f. selecting, in response to said detected first spontaneous P wave, a duration as a window of Detection of Acceleration of the Atrial Rhythm (DAAR), said selected duration being one of a first duration corresponding to said determined atrial rhythm preceding said detected first spontaneous P wave representing a fast atrial rhythm and a second duration corresponding to said determined atrial rhythm preceding said detected first spontaneous P wave representing a slow atrial rhythm;

g. initiating, in response to the detection of said first spontaneous P wave, the selected DAAR window;

h. detecting a next spontaneous P wave subsequent to said detected first spontaneous P wave;

i. initiating an atrial escape interval (AEI) in response to said detected next spontaneous P wave, j. determining whether or not the detected next spontaneous P wave is detected during the initiated selected DAAR window; and k. in response to said detected next spontaneous P wave being detected during said DAAR window, stimulating if necessary the ventricle at the end of the AEI.

17. The process of claim 16 further comprising providing a threshold wherein step f of further comprises:

comparing the determined atrial rhythm to the threshold;

providing the first duration in response to the determined atrial rhythm being greater than the threshold; and providing the second duration in response to the determined atrial rhythm not being greater than the threshold.

18. The process of claim 17 wherein providing the first duration further comprises selecting the first duration as a fraction of said determined atrial rhythm.

19. The process of claim 17 wherein:

comparing the determined atrial rhythm to the threshold further comprises determining an average atrial rhythm for a predetermined number of intervals separating two preceding successive spontaneous atrial depolarizations; and providing the first duration further comprises selecting the first duration as a fraction of said determined average atrial rhythm.

20. The process of claim 17 wherein providing the second duration further comprises selecting the second duration as a fraction of said determined atrial rhythm.

21. The process of claim 17 wherein:

comparing the determined atrial rhythm to the threshold further comprises determining an average atrial rhythm for a predetermined number of intervals separating two preceding successive spontaneous atrial depolarizations; and providing the second duration further comprises selecting the second duration as a fraction of said determined average atrial rhythm.

22. The process of claim 17 wherein:

providing the first duration further comprises selecting the first duration as a first fraction of said determined atrial rhythm; and providing the second duration further comprises selecting the second duration as a second fraction of said determined atrial rhythm, wherein the first fraction is greater than the second fraction.

23. The process of claim 22 further comprising selecting the first fraction to be approximately 75% and selecting the second fraction to be approximately 62.5%.

24. The process of claim 17 wherein:

comparing the determined atrial rhythm to the threshold further comprises determining an average atrial rhythm for a predetermined number of intervals separating two preceding successive spontaneous atrial depolarizations;

providing the first duration further comprises selecting the first duration as a first fraction of said determined average atrial rhythm; and providing the second duration further comprises selecting the second duration as a second fraction of said determined average atrial rhythm, the second fraction being greater than the first fraction.

25. The process of claim 24 further comprising selecting the first fraction to be approximately 75% and selecting the second fraction to be approximately 62.5%.

26. The process of claim 16 further comprising:

1. in response to said detected next spontaneous P wave not being detected during said DAAR window:

i) determining that said detected next spontaneous P wave is an isolated atrial extrasystoles (AES), ii) stimulating the atrium in response to the end of the AEI, and iii) establishing a first atrio-ventricular delay (AVD); and wherein step k further comprises:

declaring a suspicion of trouble of atrial rhythm (ToAR) condition, initiating an analysis of the atrial rhythm to confirm or not the ToAR condition, and establishing a second atrio-ventricular delay (AVD), the second AVD being shorter than the first AVD.

27. The process of claim 26 further comprising determining the first AVD as a function of a determined cardiac rhythm.

28. The process of claim 26 further comprising sensing a physiological parameter of a patient corresponding to at least one of activity and effort of the patient, determining a rate responsive pacing rhythm from said sensed physiological parameter, and determining the first AVD as a function of a determined cardiac rhythm and the determined rate responsive rhythm.

29. The process of claim 28 further comprising limiting the first AVD to a preselected maximum period.

30. The process of claim 26 further comprising sensing successive ventricular stimulations and setting the second AVD to a predetermined period corresponding to a minimal interval between said successive ventricular stimulations.

31. The process of claim 16 further comprising:

1. in response to the next spontaneous P wave being detected during the DAAR window, the steps of:

detecting a third spontaneous P wave during said AEI initiated in step i, declaring a suspicion of a ToAR condition, and analyzing the atrial rhythm over a time period to confirm or not confirm the suspected ToAR condition.

32. The process of claim 31, wherein the analyzing step of step 1. further comprises:

i) monitoring a number M1 of successive (atrial) cardiac cycles according to steps e-1 and determining whether or not each of said M1 successive atrial cycles is declared a suspicion of a ToAR condition;

ii) determining a first number of said M1 cardiac cycles satisfying the suspected ToAR condition;

iii) monitoring a number M2 of successive cardiac cycles according to steps e-1 and determining whether or not each of said M2 successive cardiac cycles is declared a suspicion of a ToAR condition, iv) determining a second number of said M2 cardiac cycles satisfying the suspected ToAR condition, M2 being greater than M1, v) determining that the suspected ToAR condition is confirmed in response to one of:
   1) the first number being a first majority percentage $x_1\%$ of the number M1 successive cardiac cycles, and
   2) the second number being a second majority percentage $x_2\%$ of the number M2 successive cardiac cycles, the $x_2\%$ being less than the $x_1\%$, and vi) in response to a confirmed ToAR condition, operating the pacemaker in the fallback mode, wherein the ventricular stimulation is desynchronized to the atrial rhythm.

33. The process of claim 32 further comprising selecting M2 to be twice as large as M1, $x_1\%$ to be approximately 87.5 percent, and $x_2\%$ to be approximately 56 percent.

34. The process of claim 31, wherein in response to the analyzing step of step 1 confirming a ToAR condition, said method further comprises:

desynchronizing the ventricular stimulation from the atrial rhythm;

analyzing the atrial rhythm and determining whether or not the ToAR condition is maintained; and in response to determining that the ToAR condition is not maintained:

commuting the pacemaker to operate in a mode of progressive resynchronization of the ventricular stimulation with the atrial rhythm, initiating an analysis of the ventricular rhythm and atrial rhythm and confirmation of the disappearance of the ToAR condition, and in response to the confirmation of the disappearance of the ToAR condition, commuting the pacemaker to operate in a synchronized dual chamber pacing mode.

* * * * *

UNITED STATES PATENT AND TRADEMARK OFFICE
CERTIFICATE OF CORRECTION

PATENT NO. : 5,713,928
DATED : February 3, 1998
INVENTOR(S) : Bonnet et al.

It is certified that error appears in the above-identified patent and that said Letters Patent is hereby corrected as shown below:

Abstract, line 10, after "function" insert --of--;
Column 2, line 16, before "the" insert --to--;
Column 8, line 11, after "$M_2$", delete "32" and insert -- = --.

Signed and Sealed this

Second Day of March, 1999

Attest:

Q. TODD DICKINSON

Attesting Officer          Acting Commissioner of Patents and Trademarks